Nov. 17, 1959 W. E. SILVA Plant Pat. 1,879
ROSE PLANT
Filed Feb. 11, 1959
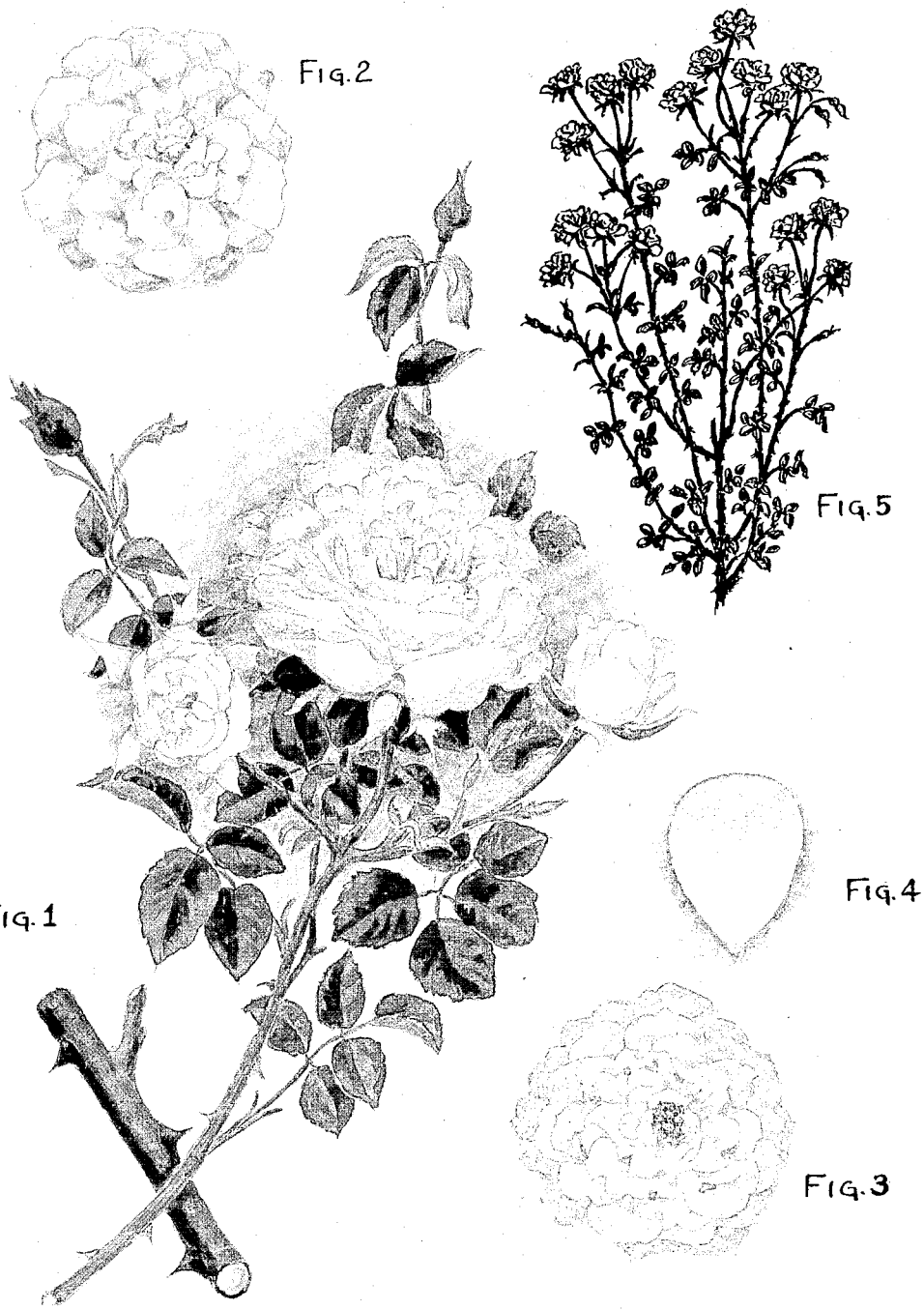
WITNESS
Addison E. Avery
INVENTOR
WILLIAM E. SILVA
by Rummler & Snow
ATTYS.

United States Patent Office

Plant Pat. 1,879
Patented Nov. 17, 1959

1,879

ROSE PLANT

William Edward Silva, Sebastopol, Calif., assignor to Plant Hybridizers of California, Sebastopol, Calif., a partnership Application February 11, 1959, Serial No. 792,685

1 Claim. (Cl. 47—61)

My present invention concerns a new and distinct variety of rose plant of the floribunda class, and is the result of definite breeding efforts carried out by me since 1948 in my rose gardens at Sebastopol, California.

My new rose plant variety is a selected seedling developed by cross breeding of the seed parent Pinnocchio (Plant Patent No. 484) with the pollen parent Crimson Glory (Plant Patent No. 105) and the new variety has been reproduced asexually by me at Sebastopol, California, whereby its novel and distinctive characteristics have been found to hold true from generation to generation and to appear permanently fixed. Asexual reproduction of my new variety has been done by budding at Sebastopol, California, and at the present time extensive propagation of the new variety is being done at San Jacinto, California.

The distinctive and unusual qualities of this new variety reside in the pompon type of its multi-colored flowers the colors of which change continuously from the bud to the full opened bloom; its prolific and continuous blooming habit; and its growth habit wherein the flowers appear in clumps on a low growing bush, whereby the continuously changing colors of the blooms produces a kaleidoscopic effect in the over-all blooming plant.

My new variety of floribunda type of rose plant blooms profusely and continuously throughout the year, the many petals of its pompon type flower staying on the stem until the flower has completely bloomed out, or about two weeks, and the flower is fragrant throughout its life. The bud is a yellowish pink color when the sepals first divide and this color turns to an orchid pink when the petals begin to unfurl. When the flower is opened, the color is a rich yellow with a tinge of pink throughout, and as the flower matures or becomes older the petals turn more pink around the margins while the yellow color fades. As the age of the flower progresses the petals have red tips and margins with about half the petal being white and the other half red, the white being at the base of the petals and the red becoming deeper in color as it approaches the tips. The matured petals are translucent and when viewed from the back the red can be seen through the petals. In partial shade the flowers are of a slightly lighter color.

The lasting quality of the flowers is very good both on the plant and as a cut flower, and the flowers are not effected by wet or hot weather. Also the new variety has been carefully observed and tested both at Sebastopol and at San Jacinto, California, and has been observed to be resistant to the common rose diseases, such as black spot, mildew and canker. No diseases have been observed in the trials and tests of this new variety, and it is therefore believed that resistance to common rose diseases is inherent in the new variety.

In the accompanying drawing illustrating the distinctive characteristics of my new variety of rose plant:

Figure 1 is a view in full color showing the foilage and wood together with buds, newly opened buds, and a fully matured bloom;

Fig. 2 is a face view of a fully opened flower showing how the initial yellowish color fades to white in the body of the petals and to a pale pink at the tips of the petals;

Fig. 3 shows a face view of a semi-mature flower showing the transition of color change from pale pink to a deeper pink in the petal margins and the outer portion of the petals;

Fig. 4 is an inside surface view of a petal from the fully mateured bloom shown in Figure 1; and Fig. 5 is a pen and ink sketch illustrating the general form and arrangement of a typical bush or full plant.

Other features of novelty in my new variety of floribunda rose will appear more particularly in the following detailed description of the new plant:

*Flower*

Blooming habit: Continuously and profusely from early spring through late fall.

Size: Medium—about 2 inches in diameter and about 1¼ inches deep.

Form: Rather flat and form does not change as the flower matures.

Petalage: 37 to 40 petals in imbricated arrangement and of obovoid, pointed tip form.

Petaloids: 10 to 12 in number and of ¼ to ½ inch in size.

Peduncle: Sturdy and upright and from 2 to 3 inches in length.

Texture: Soft.

Appearance: Velvety.

Discoloration: Begins to brown after full bloom matures.

*Bud*

Size: Approximately ½ inch.

Form: Semi-globular, urn shaped in form, diameter and depth approximately ½ inch.

Sepals: Upstanding, branched, and hooded over the bud. The bud opens slowly and the sepals curl back after the bloom. Sepals are of tomentose white color on the inside and are a reddish brown color outside.

Calyx: Pear shaped and does not split. Has slightly hairy aspect and is from ¼ to ½ inch in both breadth and length.

Peduncle: Erect, stout, about 2 to 3 inches long, and very slightly hairy. The color is green.

*Plant*

Form: Bush.

Height: 1½ to 2 feet.

Growth: Vigorous and branching, upright and sturdy, with good strength.

Foilage: Medium in quantity with pinnately compound shape of leaf 1¼ to 1½ inches long, serrated and ovoid in form.

*Texture.*—Smooth and glossy with prominent ribs and veins.

*Rachis.*—Sturdy, 2 to 3 inches long.

*Petioles.*—About ⅛ inch in length.

*Thorns.*—Young thorns about ⅛ inch long, mature thorns about ¼ inch long.

*Genital organs*

Stamens:

*Anthers.*—Approximately 30, ¼ inch long and in whorled arrangement.

*Filaments.*—¼ inch long and yellow in color.

Pollen: Orange yellow in color.

Pistils: Approximately 10 to 15 in number and ⅛ inch in length.

Stigmas: Brownish color.

Ovaries: Typical globose rose hypanthium, enclosing achenes.

*Fruit*

Fertile.

The color characteristics of my new variety of rose plant, according to Maerz and Pauls Dictionary of Color, are as follows:

| | Plate | Letter | No. |
|---|---|---|---|
| Bud (Fig.): | | | |
| pale orange yellow petals | 9 | B | 3 |
| varying from | 9 | A | 5 |
| to | 9 | I | 7 |
| Flower: | | | |
| upon first opening (Fig. 2)— | | | |
| large white medial petals | 1 | A | 1 |
| center yellowish petals | 9 | K | 4 |
| outer petals—pale pink tips | 1 | C | 1 |
| ranging to | 1 | D | 4 |
| Semi-matured (Fig. 3)— | | | |
| Outer rows of petals—pale pink | 1 | G | 7 |
| to | 1 | J | 7 |
| Inner rows—pale orange yellow | 9 | B | 3 |
| to | 9 | D | 6 |
| Fully matured (Figs. 2 and 4), mainly white petals— | | | |
| having scarlet red tip end margins | 1 | A | 1 |
| fading to pale pink toward middle portion | 1 | F | 7 |
| with pale yellow at base end | 9 | K | 1 |
| Leaf: | | | |
| Top side | 23 | L | 10 |
| Underside | 22 | D | 6 |
| Stem: | | | |
| Young | 21 | L | 6 |
| Heavy wood | 21 | L | 8 |
| Thorns: | | | |
| Young | 6 | A | 11 |
| Mature | 8 | A | 5 |

Having thus disclosed my new rose plant variety, I claim:

A new and distinct variety of rose plant of the floribunda type, substantially as herein shown and described, characterized as to novelty by the continuously changing color of its blooms from bud to fully matured flower, whereby freshly opened buds are of pale yellow color with a tinge of pink throughout turning to semi-mature flowers having white petals with pink outer end portions which petal portions turn to a deeper pink and then to red margins as the flower comes to full maturity; and further characterized by its sturdy, relatively low growth habit, and by its continuous and profuse flowering habit from early spring until late fall.

No references cited.